United States Patent [19]
Barker et al.

[11] Patent Number: 5,814,630
[45] Date of Patent: Sep. 29, 1998

[54] QUINAZOLINE COMPOUNDS

[75] Inventors: Andrew John Barker; Craig Johnstone, both of Macclesfield, United Kingdom

[73] Assignee: Zeneca Limited, London, United Kingdom

[21] Appl. No.: 800,830

[22] Filed: Feb. 13, 1997

[30]      Foreign Application Priority Data

Feb. 14, 1996 [GB] United Kingdom .................... 9603097

[51] Int. Cl.⁶ ...................... A61K 31/505; A61K 31/495; C07D 403/02; C07D 401/02
[52] U.S. Cl. ...................... 514/234.5; 514/253; 514/254; 514/259; 544/122; 544/284; 544/293
[58] Field of Search .................................... 544/284, 293, 544/122; 514/234.5, 253, 254, 259

[56]                References Cited

U.S. PATENT DOCUMENTS

| | | | |
|---|---|---|---|
| 3,266,990 | 8/1966 | Lutz et al. ............................... | 544/284 |
| 4,343,940 | 8/1982 | Kreighbaum et al. ................... | 544/283 |
| 5,580,870 | 12/1996 | Barker et al. ......................... | 514/234.5 |
| 5,616,582 | 4/1997 | Barker ................................. | 514/234.5 |

FOREIGN PATENT DOCUMENTS

| | | |
|---|---|---|
| 0 326 330 A2 | 8/1989 | European Pat. Off. . |
| 0 520 722 A1 | 12/1992 | European Pat. Off. . |
| 0 566 226 A1 | 10/1993 | European Pat. Off. . |
| 0 602 851 A1 | 6/1994 | European Pat. Off. . |
| 0 635 498 A1 | 1/1995 | European Pat. Off. . |
| 0 635 507 A1 | 1/1995 | European Pat. Off. . |
| 0 682 027 A1 | 11/1995 | European Pat. Off. . |
| 0 326 307 | 2/1996 | European Pat. Off. . |
| 0 787 722 A1 | 8/1997 | European Pat. Off. . |
| 19528672 | 2/1997 | Germany . |
| 2 033 894 | 5/1980 | United Kingdom . |
| 2 160 201 | 12/1985 | United Kingdom . |
| WO 92/14716 | 9/1992 | WIPO . |
| WO 92/20642 | 11/1992 | WIPO . |
| WO 95/06648 | 3/1995 | WIPO . |
| WO 95/15758 | 6/1995 | WIPO . |
| WO 95/15952 | 6/1995 | WIPO . |
| WO 95/19169 | 7/1995 | WIPO . |
| WO 95/19774 | 7/1995 | WIPO . |
| WO 95/19970 | 7/1995 | WIPO . |
| WO 95/21613 | 8/1995 | WIPO . |
| WO 95/23141 | 8/1995 | WIPO . |
| WO 95/24190 | 9/1995 | WIPO . |
| WO 96/07657 | 3/1996 | WIPO . |
| WO 96/09294 | 3/1996 | WIPO . |
| WO 96/15118 | 5/1996 | WIPO . |
| 96/16960 | 6/1996 | WIPO . |
| WO 96/16960 | 6/1996 | WIPO . |
| WO 96/29333 | 9/1996 | WIPO . |
| WO 96/30347 | 10/1996 | WIPO . |
| WO 96/31510 | 10/1996 | WIPO . |
| WO 96/33977 | 10/1996 | WIPO . |
| WO 96/33978 | 10/1996 | WIPO . |
| WO 96/33979 | 10/1996 | WIPO . |
| WO 96/33980 | 10/1996 | WIPO . |
| WO 96/33981 | 10/1996 | WIPO . |
| WO 96/34867 | 11/1996 | WIPO . |
| WO 96/35689 | 11/1996 | WIPO . |
| WO 96/39145 | 12/1996 | WIPO . |
| WO 96/40142 | 12/1996 | WIPO . |
| WO 96/40648 | 12/1996 | WIPO . |
| WO 97/02266 | 1/1997 | WIPO . |
| WO 97/3069 | 1/1997 | WIPO . |
| WO 97/13760 | 4/1997 | WIPO . |
| WO 97/13771 | 4/1997 | WIPO . |
| WO 97/18212 | 5/1997 | WIPO . |

OTHER PUBLICATIONS

Rewcastle et al., "Tyrosine Kinase Inhibitors. 5. Synthesis and Structure–Activity Relationships for 4–[(Phenylmethyl)amino ]–and 4–(Phenylamino)quinazolines as Potent Adenosine 5'–Triphosphate Binding Site Inhibitors of the Tyrosine Kinase Domain of the Epidermal Growth Factor Receptor," J.Med.Chem. 1995, vol. 38, pp. 3482–3487.

Burke, Jr., "Protein–tyrosine kinase inhibitors," Drugs of the Future 1992, vol. 17(2), pp. 119–131.

Spence, "Inhibitors of Tyrosine Kinase Activity as Anticancer Therapeutics: Recent Developments," Current Opinion in Therapeutic Patents, Jan. 1993, Patent Update, Anticancers, etc., pp. 3–9, Current Drugs Ltd ISSN 0962–2594,.

Spada, et al., "Small molecule inhibitors of tyrosine Kinase activity, Exp.Opin.Ther.Patents (1995), 5(8):805–817, Patent Update, Oncologic, Endocrine & Metabolic, Ashley Publications Ltd ISSN 1354–3776.

Bridges, "The current status of tyrosine kinase inhibitors: do the diarylamine inhibitors of the EGF receptor represent a new beginning?," Exp.Opin.Ther.Patents (1995), 5(12): 1245–1257, Editorial, Oncologic, Endocrine & Metabolic, 1995 Ashley Publications Ltd ISSN 1354–3776.

(List continued on next page.)

*Primary Examiner*—Matthew V. Grumbling
*Attorney, Agent, or Firm*—Cushman Darby & Cushman Intellectual Property Group of Pillsbury Madison & Sutro, LLP

[57]                ABSTRACT

The invention concerns quinazoline compounds of the formula I

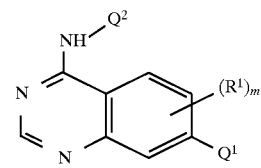

wherein $Q^1$ is a 5- or 6-membered heteroaryl moiety and $Q^1$ optionally bears up to 3 substituents;

wherein m is 1 or 2 and each $R^1$ may be a group such as hydrogen, halogeno and trifluoromethyl;

and wherein $Q^2$ is phenyl which optionally bears up to 3 substituents; or a pharmaceutically-acceptable salt thereof;

processes for their preparation, pharmaceutical compositions containing them and the use of their receptor tyrosine kinase inhibitory properties in the treatment of proliferative disease such as cancer.

7 Claims, No Drawings

OTHER PUBLICATIONS

Traxler, et al., "Recent advances in protein tyrosine kinase inhibitors," Drugs of the Future 1995, vol. 20(12, pp. 1261–1274.

Iyer, et al., "Studies in Potential Amoebicides: Part III–Synthesis of $_4$–Substituted Amino–8–Hydroxy) Quinazolines & $_3$–Substituted 8–Hydroxy(&8–Methoxy)–$_4$–Quinazolones," J.Sci.Industr.Res., vol. 15C, Jan. 1956, pp. 1–7.

Derwent Abstract 82–87077, vol. 6, No. 244, Dec. 1982, JP 57–144266, Kobayashi, Sep. 1982, "4–Anilinoquinazoline Derivative, its Preparation and Analgesic and Antiphlogistic Agent Containing Said Derivative as Active Component".

Derwent Abstract 81–28290, JP 56–20577, Feb. 1981, Sankyo and Ube, "4–(N–alkyl:anilino) quinazoline derivs . . . having analgesic and antiinflammatory actions".

Derwent Abstract 84–53835, JP 59–13765, Jan. 1984, Kyorin, "2–(4–Quinazolinyl)amino benzoic acid derivs . . . having analgesic and antiinflammatory activities".

Chem.Abs., vol. 92:76445u, 1980, pp. 674–675, Li, et al.

Chem.Abs., vol. 96:122728w, 1982, p. 695, Lin et al.

Fry et al., "Specific Inhibitor of the Epidermal Growth Factor Receptor Tyrosine Kinase," Science, vol. 265, Aug. 19, 1994, pp. 1093–1095.

Buchdunger, et al., "4,5–Dianilinophthalimide: A protein–throsine kinase inhibitor with selectivity for the epidermal growth factor receptor signal transduction pathway and potent in vivo antitumor activity," Prac.Natl.Acad.Sci., USA, vol. 91, pp. 2334–2338, Mar. 1994, Applied Biological Sciences.

Trinks, et al., "Dianilinophthalimides: Potent and Selective, ATP–Competitive Inhibitors of the EGF–Receptor Protein Tyrosine Kinase," J.Med. Chem. 1994, vol. 37, pp. 1015–1027.

Maguire, et al., "A New Series of PDGF Receptor Tyrosine Kinase Inhibitors: 3–Substituted Quinoline Derivatives," J.Med.Chem. 1994, vol. 37, pp. 2129–2137.

Dolle, et al., "5,7–Demethoxy–3–(4–pyridinyl)quinoline Is a Potent and Selective Inhibitor of Human Vascular β–Type Platelet–Derived Growth Factor Receptor Tyrosine Kinase," J.Med.Chem. 1994, vol. 37, pp. 2627–2629.

Ward, et al., "Epidermal Growth Factor Receptor Tyrosine Kinase—Investigation of Catalytic Mechanism, Structure-–Based Searching and Discovery of a Potent Inhibitor," Biochem.Pharmacology, vol. 48, No. 4, pp. 659–666 (1994).

Ward, et al., "Epidermal Growth Factor Receptor Tyrosine Kinase—Investigation of Catalytic Mechanism, Structure-–Based Searching and Discovery of a Potent Inhibitor," Biochem.Pharmacology, vol. 48, No. pp. 659–666 (1994).

Connolly, et al., "Human Vascular Permeablility Factor," J.Bio.Chem., vol. 264, No. 33, Nov. 1989 , pp. 20017–20024.

Cullinan–Bove, et al., "Vascular Endothelial Growth Factor/ Vascular Permeablility Factor Expression in the Rat Uterus . . . ," Endocrinology, vol. 133, No. 2, 1993, pp. 829–837.

Fan, et al., "controlling the Vasculature: Angiogenesis, Anti-Angiogenesis . . . ," TiPS Review, vol. 16, Feb. 1995, pp. 57–65.

Folkman, "Angiogenesis in Cancer, Vascular, Rheumatoid and Other Disease," Nature Medicine, vol. 1, No. 1, 1995, pp. 27–30.

Jakeman, et al., "Developmental Expression of Binding Sites and Messenger Ribonucleic Acid . . . ," Endocrinology, vol. 133, No. 2, 1993, pp. 848–859.

Kim, et al., "Inhibition of Vascular Endothelial Growth Factor–Induced Angiogenesis Suppresses Tumour Growth in Vivo," Nature, vol. 362, Apr. 1993, pp. 841–844.

Kolch, et al., "Regulation of the Expression of the VEGF/ VPS and its Receptors: Role in Tumor Angiogenesis," Breast Cancer Research and Treatment, vol. 36, 1995, pp. 139–155.

Senger, et al., "Vascular Permeablility Factor (VPF, VEGF) in Tumor Biology," Cancer and Metastasis Reviews, vol. 12, 1993, pp. 303–324.

QUINAZOLINE COMPOUNDS

The invention relates to quinazoline compounds, or pharmaceutically-acceptable salts thereof, which possess anti-proliferative activity such as anti-cancer activity and are accordingly useful in methods of treatment of the human or animal body. The invention also relates to processes for the manufacture of said quinazoline compounds, to pharmaceutical compositions containing them and to their use in the manufacture of medicaments for use in the production of an anti-proliferative effect in a warm-blooded animal such as man.

Many of the current treatment regimes for cell proliferation diseases such as psoriasis and cancer utilise compounds which inhibit DNA synthesis. Such compounds are toxic to cells generally but their toxic effect on rapidly dividing cells such as tumour cells can be beneficial. Alternative approaches to anti-proliferative agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis* 1986, 1, 91). Several such oncogenes give rise to the production of peptides which are receptors for growth factors. The growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al. *Ann. Reports in Med. Chem.* 1989, Chpt. 13).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43–73) based on families of growth factors which bind to different receptor tyrosine kinases. The classification includes Class I receptor tyrosine kinases comprising the EGF family of receptor tyrosine kinases such as the EGF, transforming growth factor α (TGFα), NEU, erbB, Xmrk, DER and let23 receptors, Class II receptor tyrosine kinases comprising the insulin family of receptor tyrosine kinases such as the insulin, IGFI and insulin-related receptor (IRR) receptors and Class III receptor tyrosine kinases comprising the platelet-derived growth factor (PDGF) family of receptor tyrosine kinases such as the PDGFα, PDGFβ and colony-stimulating factor 1 (CSF1) receptors. It is known that Class I kinases such as the EGF family of receptor tyrosine kinases are frequently present in common human cancers such as breast cancer (Sainsbury et al., *Brit. J. Cancer,* 1988, 58, 458; Guerin et al., *Oncogene Res.,* 1988, 3, 21, and Klijn et al., *Breast Cancer Res. Treat.,* 1994, 29, 73), non-small cell lung cancers (NSCLCs) including adenocarcinomas (Cerny et al., *Brit. J. Cancer,* 1986, 54, 265; Reubi et al., *Int. J. Cancer* 1990, 45, 269 and Rusch et al., *Cancer Research,* 1993, 53, 2379) and squamous cell cancer of the lung (Hendler et al., *Cancer Cells,* 1989, 7, 347), bladder cancer (Neal et al., *Lancet,* 1985, 366), oesophageal cancer (Mukaida et al., *Cancer* 1991, 68, 142), gastrointestinal cancer such as colon, rectal or stomach cancer (Bolen et al., *Oncogene Res.,* 1987, 1, 149), cancer of the prostate (Visakorpi et al., *Histochem. J.,* 1992, 24, 481), leukaemia (Konaka et al., *Cell,* 1984, 37, 1035) and ovarian, bronchial or pancreatic cancer (European Patent Specification No. 0400586). As further human tumour tissues are tested for the EGF family of receptor tyrosine kinases it is expected that its widespread prevalance will be established in further cancers such as thyroid and uterine cancer. It is also known that EGF type tyrosine kinase activity is rarely detected in normal cells whereas it is more frequently detectable in malignant cells (Hunter, *Cell,* 1987, 50, 823). It has been shown more recently (W. J. Gullick, *Brit. Med. Bull.,* 1991, 47, 87) that EGF receptors which possesses tyrosine kinase activity are overexpressed in many human cancers such as brain, lung squamous cell, bladder, gastric, colorectal, breast, head and neck, oesophageal, gynaecological and thyroid tumours.

Accordingly it has been recognised that an inhibitor of receptor tyrosine kinases should be of value as a selective inhibitor of the growth of mammalian cancer cells (Yaish et al. *Science,* 1988, 242, 933). Support for this view is provided by the demonstration that erbstatin, an EGF receptor tyrosine kinase inhibitor, specifically attenuates the growth in athymic nude mice of a transplanted human mammary carcinoma which expresses EGF receptor tyrosine kinase but is without effect on the growth of another carcinoma which does not express EGF receptor tyrosine kinase (Toi et al., *Eur. J. Cancer Clin. Oncol.,* 1990, 26, 722). Various derivatives of styrene are also stated to possess tyrosine kinase inhibitory properties (European Patent Application Nos. 0211363, 0304493 and 0322738) and to be of use as anti-tumour agents. The in vivo inhibitory effect of two such styrene derivatives which are EGF receptor tyrosine kinase inhibitors has been demonstrated against the growth of human squamous cell carcinoma inoculated into nude mice (Yoneda et al., *Cancer Research,* 1991, 51, 4430). Accordingly it has been indicated that Class I receptor tyrosine kinase inhibitors will prove to be useful in the treatment of a variety of human cancers. Various known tyrosine kinase inhibitors are disclosed in a more recent review by T. R. Burke Jr. (*Drugs of the Future,* 1992, 17, 119).

EGF type receptor tyrosine kinases have also been implicated in non-malignant proliferative disorders such as psoriasis (Elder et al., *Science,* 1989, 243, 811). It is therefore expected that inhibitors of EGF type receptor tyrosine kinases will be useful in the treatment of non-malignant diseases of excessive cellular proliferation such as psoriasis (where TGFα is believed to be the most important growth factor), benign prostatic hypertrophy (BPH), atherosclerosis and restenosis.

It is known from European Patent Applications Nos. 0520722 and 0566226 and from International Patent Applications WO 95/15758, WO 95/19169, WO 96/09294, WO 96/15118, WO 96/16960 and WO 96/30347 that certain quinazoline derivatives which bear an anilino substituent at the 4-position possess receptor tyrosine kinase inhibitory activity. It is further known from European Patent Application No. 0602851 and from International Patent Application WO 95/23141 that certain quinazoline derivatives which bear a heteroarylamino substituent at the 4-position also possess receptor tyrosine kinase inhibitory activity.

It is further known from International Patent Application WO 92/20642 that certain aryl and heteroaryl compounds inhibit EGF and/or PDGF receptor tyrosine kinase. There is the disclosure of certain quinazoline derivatives therein but no mention is made of 4-anilinoquinazoline derivatives.

It is further known from European Patent Application No. 0635507 and from International Patent Applications WO 95/06648, WO 95/19970 and WO 96/29331 that certain tricyclic compounds which comprise a 5- or 6-membered ring fused to the benzo-ring of a quinazoline possess receptor tyrosine kinase inhibitory activity or phosphodiesterase inhibitory activity. It is also known from European Patent Application No. 0635498 that certain quinazoline derivatives which carry an amino group at the 6-position and a halogeno group at the 7-position possess receptor tyrosine kinase inhibitory activity.

The in vitro anti-proliferative effect of a 4-anilinoquinazoline derivative has been disclosed by Fry et al., Science, 1994, 265, 1093. It was stated that the compound 4-(3-bromoanilino)-6,7-dimethoxyquinazoline was a highly potent inhibitor of EGF receptor tyrosine kinase.

The in vivo inhibitory effect of a 4,5-dianilinophthalimide derivative which is an inhibitor of the EGF family of receptor tyrosine kinases has been demonstrated against the growth in BALB/c nude mice of a human epidermoid carcinoma A-431 or of a human ovarian carcinoma SKOV-3 (Buchdunger et al., Proc. Nat. Acad. Sci., 1994, 91, 2334).

It is further disclosed in International Patent Applications WO 96/33977, WO 96/33978, WO 96/33979, WO 96/33980 and WO 96/33981 that certain further quinazoline derivatives which bear an anilino substituent at the 4-position possess receptor tyrosine kinase inhibitory activity.

There is no disclosure in these documents of quinazoline derivatives which bear a heteroaryl moiety attached directly to the 7-position.

We have now found that such compounds possess anti-proliferative properties which are believed to arise from their Class I (EGF type) receptor tyrosine kinase inhibitory activity.

According to the invention there is provided a quinazoline compound of the formula I

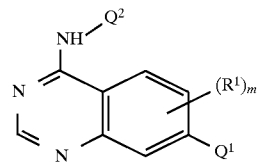

I wherein $Q^1$ is a 5- or 6-membered heteroaryl moiety containing up to 3 heteroatoms selected from oxygen, nitrogen and sulphur, which heterocyclic moiety is a single ring or is fused to a benzo ring, and $Q^1$ optionally bears up to 3 substituents selected from halogeno, hydroxy, amino, trifluoromethyl, cyano, nitro, carboxy, carbamoyl, (1–4C)alkoxycarbonyl, (1–4C)alkyl, (1–4C)alkoxy, (1–4C)alkylamino, di-[(1–4C)alkyl]amino, pyrrolidin-1-yl, piperidino, morpholino, piperazin-1-yl, 4-(1–4C)alkylpiperazin-1-yl, (2–4C)alkanoylamino, N-(1–4C)alkylcarbamoyl, N,N-di-[(1–4C)alkyl]carbamoyl, amino-(1–4C)alkyl, (1–4C)alkylamino-(1–4C)alkyl, di-[(1–4C)alkyl]amino-(1–4C)alkyl, pyrrolidin-1-yl-(1–4C)alkyl, piperidino-(1–4C)alkyl, morpholino-(1–4C)alkyl, piperazin-1-yl-(1–4C)alkyl, 4-(1–4C)alkylpiperazin-1-yl-(1–4C)alkyl, halogeno-(2–4C)alkoxy, hydroxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, pyrrolidin-1-yl-(2–4C)alkoxy, piperidino-(2–4C)alkoxy, morpholino-(2–4C)alkoxy, piperazin-1-yl-(2–4C)alkoxy, 4-(1–4C)alkylpiperazin-1-yl-(2–4C)alkoxy, (1–4C)alkylthio-(2–4C)alkoxy, (1–4C)alkylsulphinyl-(2–4C)alkoxy, (1–4C)alkylsulphonyl-(2–4C)alkoxy, halogeno-(2–4C)alkylamino, hydroxy-(2–4C)alkylamino, (1–4C)alkoxy-(2–4C)alkylamino, amino-(2–4C)alkylamino, (1–4C)alkylamino-(2–4C)alkylamino, di-[(1–4C)alkyl]amino-(2–4C)alkylamino, pyrrolidin-1-yl-(2–4C)alkylamino, piperidino-(2–4C)alkylamino, morpholino-(2–4C)alkylamino, piperazin-1-yl-(2–4C)alkylamino, 4-(1–4C)alkylpiperazin-1-yl-(2–4C)alkylamino, N-(1–4C)alkyl-halogeno-(2–4C)alkylamino, N-(1–4C)alkyl-hydroxy-(2–4C)alkylamino, N-(1–4C)alkyl-(1–4C)alkoxy-(2–4C)alkylamino, halogeno-(2–4C)alkanoylamino, hydroxy-(2–4C)alkanoylamino, (1–4C)alkoxy-(2–4C)alkanoylamino, (3–4C)alkenoylamino, (3–4C)alkynoylamino, amino-(2–4C)alkanoylamino, (1–4C)alkylamino-(2–4C)alkanoylamino, di-[(1–4C)alkyl]amino-(2–4C)alkanoylamino, pyrrolidin-1-yl-(2–4C)alkanoylamino, piperidino-(2–4C)alkanoylamino, morpholino-(2–4C)alkanoylamino, piperazin-1-yl-(2–4C)alkanoylamino and 4-(1–4C)alkylpiperazin-1-yl-(2–4C)alkanoylamino, and wherein any of the above-mentioned substituents comprising a $CH_2$ (methylene) group which is not attached to a halogeno, $SO$ or $SO_2$ group or to a N, O or S atom optionally bears on said $CH_2$ group a substituent selected from hydroxy, amino, (1–4C)alkoxy, (1–4C)alkylamino and di-[(1–4C)alkyl]amino;

wherein m is 1 or 2 and each $R^1$ is independently hydrogen, halogeno, trifluoromethyl, hydroxy, amino, nitro, cyano, carboxy, carbamoyl, (1–4C)alkoxycarbamoyl, (1–4C)alkyl, (1–4C)alkoxy, (1–4C)alkylamino, di-[(1–4C)alkyl]amino, (2–4C)alkanoylamino, N-(1–4C)alkylcarbamoyl or N,N-di-[(1–4C)alkyl]carbamoyl;

and wherein $Q^2$ is phenyl which optionally bears up to 3 substituents selected from halogeno, trifluoromethyl, cyano, hydroxy, amino, nitro, carboxy, carbamoyl, (1–4C)alkoxycarbonyl, (1–4C)alkyl, (1–4C)alkoxy, (1–4C)alkylamino, di-[(1–4C)alkyl]amino, (2–4C)alkanoylamino, N-(1–4C)alkylcarbamoyl and N,N-di-(1–4C)alkylcarbamoyl;

or a pharmaceutically-acceptable salt thereof.

In this specification the term "alkyl" includes both straight and branched chain alkyl groups but references to individual alkyl groups such as "propyl" are specific for the straight chain version only. For example when $R^1$ is a hydroxy-(2–4C)alkoxy group, suitable values for this generic radical include 2-hydroxyethoxy, 2-hydroxypropoxy, 1-hydroxyprop-2-yloxy and 3-hydroxypropoxy. An analogous convention applies to other generic terms.

Within the present invention it is to be understood that a quinazoline compound of the formula I may exhibit the phenomenon of tautomerism and that the formulae drawings within this specification can represent only one of the possible tautomeric forms. It is to be understood that the invention encompasses any tautomeric form which possesses anti-proliferative activity and is not to be limited merely to any one tautomeric form utilised within the formulae drawings.

The quinazolines of the formula I are unsubstituted at the 2-position thus it is to be understood that the $R^1$ groups are located only on the benzo portion of the quinazoline ring.

It is also to be understood that certain quinazoline compounds of the formula I can exist in solvated as well as unsolvated forms such as, for example, hydrated forms. It is to be understood that the invention encompasses all such solvated forms which possess anti-proliferative activity.

Suitable values for the generic radicals referred to above include those set out below.

A suitable value for a substituent on $Q^1$ or $Q^2$, for a substituent on a $CH_2$ group within a substituent on $Q^1$, or for $R^1$ when it is halogeno is, for example, fluoro, chloro, bromo or iodo;

when it is (1–4C)alkyl is, for example, methyl, ethyl, propyl, isopropyl or butyl;

when it is (1–4C)alkoxy is, for example, methoxy, ethoxy, propoxy, isopropoxy or butoxy;

when it is (1–4C)alkylamino is, for example, methylamino, ethylamino or propylamino;

when it is di-[(1–4C)alkyl]amino is, for example, dimethylamino, diethylamino, N-ethyl-N-methylamino or dipropylamino;

when it is (2–4C)alkanoylamino is, for example, acetamido, propionamido or butyramido;

when it is (1–4C)alkoxycarbonyl is, for example, methoxycarbonyl, ethoxycarbonyl, propoxycarbonyl, butoxcarbonyl or tert-butoxycarbonyl;

when it is N-(1–4C)alkylcarbamoyl is, for example, N-methylcarbamoyl or N-ethylcarbamoyl;

and when it is N,N-di-[(1–4C)alkyl]carbamoyl is, for example, N,N-dimethylcarbamoyl, N-ethyl-N-methylcarbamoyl and N,N-diethylcarbamoyl.

Suitable values for each substituent which may be present on $Q^1$ include, for example:

| | |
|---|---|
| for 4-(1-4C)alkyl-piperazin-1-yl: | 4-methylpiperazin-1-yl and 4-ethylpiperazin-1-yl; |
| for amino-(1-4C)alkyl: | aminomethyl, 2-aminoethyl and 3-aminopropyl; |
| for (1-4C)alkylamino-(1-4C)alkyl: | methylaminomethyl, 2-methylaminoethyl and 3-methylaminopropyl; |
| for di-[(1-4C)alkyl]amino-(1-4C)alkyl: | dimethylaminomethyl, diethylaminomethyl, 2-dimethylaminoethyl, 2-diethylaminoethyl and 3-dimethylaminopropyl; |
| for pyrrolidin-1-yl-1-4C)alkyl: | pyrrolidin-1-ylmethyl, 2-pyrrolidin-1-ylethyl and 3-pyrrolidin-1-ylpropyl; |
| for piperidino-(1-4C)alkyl: | piperidinomethyl, 2-piperidinoethyl and 3-piperidinopropyl; |
| for morpholino-(1-4C)alkyl: | morpholinomethyl, 2-morpholinoethyl and 3-morpholinopropyl; |
| for piperazin-1-yl-(1-4C)alkyl: | piperazin-1-ylmethyl, 2-piperazin-1-ylethyl and 3-piperazin-1-ylpropyl; |
| for 4-(1-4C)alkylpiperazin-1-yl-(1-4C)alkyl: | 4-methylpiperazin-1-ylmethyl, 2-(4-methylpiperazin-1-yl)ethyl and 3-(4-methylpiperazin-1-yl)propyl; |
| for halogeno-(2-4C)alkoxy: | 2-fluoroethoxy, 2-chloroethoxy, 2-bromoethoxy, 3-fluoropropoxy, 3-chloropropoxy, 2,2,2-trifluoroethoxy, 1,1,2,2,2-pentafluoroethoxy, 2,2,3,3-tetrafluoropropoxy, 2,2,3,3,3-pentafluoropropoxy and 1,1,2,2,3,3,3-heptafluoropropoxy; |
| for hydroxy-(2-4C)alkoxy: | 2-hydroxyethoxy, 3-hydroxypropoxy and 4-hydroxybutoxy; |
| for (1-4C)alkoxy-(2-4C)alkoxy: | 2-methoxyethoxy, 2-ethoxyethoxy, 3-methoxypropoxy and 3-ethoxypropoxy; |
| for amino-(2-4C)alkoxy: | 2-aminoethoxy and 3-aminopropoxy; |
| for (1-4C)alkylamino-(2-4C)-alkoxy: | 2-methylaminoethoxy, 2-ethylaminoethoxy, 2-propylaminoethoxy, 3 methylaminopropoxy and 3-ethylaminopropoxy; |
| for di-[(1-4C)alkyl]amino-(2-4C)alkoxy: | 2-dimethylaminoethoxy, 2-(N-ethyl-N-methylamino)ethoxy, 2-diethylaminoethoxy, 2-dipropylaminoethoxy, 3-dimethylaminopropoxy and 3-diethylaminopropoxy; |
| for pyrrolidin-1-yl-(2-4C)-alkoxy: | 2-(pyrrolidin-1-yl)ethoxy and 3-(pyrrolidin-1-yl)propoxy; |
| for piperidino-(2-4C)alkoxy: | 2-piperidinoethoxy and 3-piperidinopropoxy; |
| for morpholino-(2-4C)alkoxy: | 2-morpholinoethoxy and 3-morpholinopropoxy; |
| for piperazin-1-yl-(2-4C)alkoxy: | 2-(piperazin-1-yl)ethoxy and 3-(piperazin-1-yl)propoxy; |
| for 4-(1-4C)alkylpiperazin-1-yl-(2-4C)alkoxy: | 2-(4-methyipiperazin-1-yl)ethoxy and 3-(4-methylpiperazin-1-yl)propoxy; |
| for (1-4C)alkylthio-(2-4C)alkoxy: | 2-methylthioethoxy and 3-methylthiopropoxy; |
| for (1-4C)alkylsulphinyl-(2-4C)-alkoxy: | 2-methylsulphinylethoxy and 3-methylsulphinylpropoxy; |
| for (1-4C)alkylsulphonyl-(2-4C)-alkoxy: | 2-methylsulphonylethoxy and 3-methylsulphonylpropoxy; |
| for halogeno-(2-4C)alkylamino: | 2-fluoroethylamino, 2-chloroethylamino, 2-bromoethylamino, 3-fluoropropylamino and 3-chloropropylamino; |
| for hydroxy-(2-4C)alkylamino: | 2-hydroxyethylamino, 3-hydroxypropylamino and 4-hydroxybutylamino; |
| for (1-4C)alkoxy-(2-4C)alkyl-amino: | 2-methoxyethylamino, 2-ethoxyethylamino, 3-methoxypropylamino and 3-ethoxypropylamino; |
| for amino-(2-4C)alkylamino: | 2-aminoethylamino, 3-aminopropylamino and 4-aminobutylamino; |
| for (1-4C)alkylamino-(2-4C)alkylamino: | 2-methylaminoethylamino, 2-ethyl-aminoethylamino, 2-propylaminoethylamino, 3-methylaminopropylamino, 3-ethylaminopropylamino and 4-methylaminobutylamino; |

-continued

| | |
|---|---|
| for di-[(1-4C)alkyl]amino-<br>(2-4C)alkylamino: | 2-dimethylaminoethylamino,<br>2-(N-ethyl-N-methylamino)ethylamino,<br>2-diethylaminoethylamino,<br>2-dipropylaminoethylamino,<br>3-dimethylaminopropylamino,<br>3-diethylaminopropylamino and<br>4-dimethylaminobutylamino; |
| for pyrrolidin-1-yl-(2-4C)-<br>alkylamino: | 2-(pyrrolidin-1-yl)ethylamino and<br>3-(pyrrolidin-1-yl)propylamino; |
| for piperidino-(2-4C)alkylamino: | 2-piperidinoethylamino and<br>3-piperidinopropylamino; |
| for morpholino-(2-4C)alkylamino: | 2-morpholinoethylamino and<br>3-morpholinopropylamino; |
| for piperazin-1-yl-(2-4C)-<br>alkylamino: | 2-(piperazin-1-yl)ethylamino and<br>3-(piperazin-1-yl)propylamino; |
| for 4-(1-4C)alkylpiperazin-1-yl-<br>(2-4C)alkylamino: | 2-(4-methylpiperazin-1-yl)ethylamino and<br>3-(4-methylpiperazin-1-yl)propylamino; |
| for N-(1-4C)alkyl-halogeno-<br>(2-4C)alkylamino: | N-(2-chloroethyl)-N-methylamino,<br>N-(2-bromoethyl)-N-methylamino and<br>N-(2-bromoethyl)-N-ethylamino; |
| for N-(1-4C)alkyl-hydroxy-(2-4C)-<br>alkylamino: | N-(2-hydroxyethyl)-N-methylamino,<br>N-(3-hydroxypropyl)-N-methylamino and<br>N-ethyl-N-(2-hydroxyethyl)amino; |
| for N-(1-4C)alkyl-(1-4C)alkoxy-<br>(2-4C)alkylamino: | N-methyl-N-(2-methoxyethyl)amino,<br>N-methyl-N-(3-methoxypropyl)amino and<br>N-ethyl-N-(2-methoxyethyl)amino; |
| for halogeno-(2-4C)alkanoylamino: | 2-chloroacetamido, 2-bromoacetamido,<br>3-chloropropionamido and 3-bromopropionamido; |
| for hydroxy-(2-4C)alkanoylamino: | 2-hydroxyacetamido, 3-hydroxypropionamido and<br>4-hydroxybutyramido; |
| for (1-4C)alkoxy-(2-4C)-<br>alkanoylamino: | 2-methoxyacetamido, 2-ethoxyacetamido,<br>2-propoxyacetamido, 3-methoxypropionamido,<br>3-ethoxypropionamido and 4-methoxybutyramido; |
| for (3-4C)alkenoylamino: | acrylamido, methacrylamido, crotonamido and<br>isocrotonamido; |
| for (3-4C)alkynoylamino: | propiolamido; |
| for amino-(2-4C)alkanoylamino: | 2-aminoacetamido, 2-aminopropionamido and<br>3-aminopropionamido; |
| for (1-4C)alkylamino-(2-4C)-<br>alkanoylamino: | 2-methylaminoacetamido, 2-ethylaminoacetamido,<br>2-methylaminopropionamido and<br>3-methylaminopropionamido; |
| for di-[(1-4C)alkyl]amino-(2-4C)-<br>alkanoylamino: | 2-dimethylaminoacetamido,<br>2-diethylaminoacetamido,<br>2-dimethylaminopropionamido and<br>3-dimethylaminopropionamido; |
| for pyrrolidin-1-yl-(2-4C)-<br>alkanoylamino: | 2-pyrrolidin-1-ylacetamido,<br>2-pyrrolidin-1-ylpropionamido and<br>3-pyrrolidin-1-ylpropionamido; |
| for piperidino-(2-4C)-<br>alkanoylamino: | 2-piperidinoacetamido, 2-piperidinopropionamido<br>and 3-piperidinopropionamido; |
| for morpholino-(2-4C)-<br>alkanoylamino: | 2-morpholinoacetamido,<br>2-morpholinopropionamido and<br>3-morpholinopropionamido; |
| for piperazin-1-yl-(2-4C)-<br>alkanoylamino: | 2-piperazin-1-ylacetamido,<br>2-piperazin-1-ylpropionamido and<br>3-piperazin-1-ylpropionamido; |
| for 4-(1-4C)alkylpiperazin-1-yl-<br>(2-4C)alkanoylamino : | 2-(4-methylpiperazin-1-yl)acetamido,<br>2-(4-methylpiperazin-1-yl)propionamido and<br>3-(4-methylpiperazin-1-yl)propionamido. |

When m is 1 the $R^1$ substituent is preferably located at the 6-position of the quinazoline ring.

Suitable substituents formed when any of the substituents on $Q^1$ comprising a $CH_2$ group which is not attached to a halogeno, SO or $SO_2$ group or to a N, O or S atom bears on said $CH_2$ group a substituent selected from hydroxy, amino, (1–4C)alkoxy, (1–4C)alkylamino and di-[(1–4C)alkyl]amino include, for example, substituted (1–4C)alkylamino-(2–4C)alkoxy or di-[(1–4C)alkyl]amino-(2–4C)alkoxy groups, for example hydroxy-(1–4C)alkylamino-(2–4C)alkoxy or hydroxy-di-[(1–4C)alkyl]amino-(2–4C)alkoxy groups such as 3-methylamino-2-hydroxypropoxy and 3-dimethylamino-2-hydroxypropoxy.

A suitable value for $Q^1$ when it is a 5- or 6-membered heteroaryl moiety containing up to 3 heteroatoms selected from oxygen, nitrogen and sulphur, which is a single ring is, for example, furyl, pyrrolyl, thienyl, pyridyl, oxazolyl, isoxazolyl, pyrazolyl, imidazolyl, thiazolyl, isothiazolyl, pyrazinyl, pyrimidinyl, pyridazinyl, 1,2,3-triazolyl, 1,2,4-triazolyl, oxadiazolyl, furazanyl or thiadiazoylyl, or which is fused to a benzo ring is, for example, benzofuryl, indolyl, benzothienyl, quinolyl, isoquinolyl, benzoxazolyl, indazolyl, benzimidazolyl, benzothiazolyl, cinnolinyl, quinazolinyl, quinoxalinyl or benzotriazolyl. Said heteroaryl moiety may be attached through any available position. The optional substituents on $Q^1$ may be located at any available position including on any available nitrogen heteroatom.

A suitable pharmaceutically-acceptable salt of a quinazoline compound of the invention is, for example, an acid-addition salt of a quinazoline compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a quinazoline compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention include, for example, quinazoline compounds of the formula I, or pharmaceutically-acceptable salts thereof, wherein, unless otherwise stated, each of $Q^1$, m, $R^1$ and $Q^2$ has any of the meanings defined hereinbefore or in this section concerning particular compounds of the invention:

(a) $Q^1$ is a 5- or 6-membered monocyclic heteroaryl moiety containing up to 3 heteroatoms selected from oxygen, nitrogen and sulphur which is optionally substituted as defined hereinbefore;

(b) $Q^1$ is furyl, pyrrolyl, thienyl, pyridyl, oxazolyl, isoxazolyl, pyrazolyl, imidazolyl, thiazolyl, isothiazolyl, pyrazinyl, pyrimidinyl, pyridazinyl, 1,2,3-triazolyl or 1,2,4-triazolyl which is attached from any available position including from a nitrogen atom and which is optionally substituted as defined hereinbefore;

(c) $Q^1$ bears no optional substituents;

(d) $Q^1$ bears 1 or 2 substituents selected from halogeno, hydroxy, amino, trifluoromethyl, cyano, nitro, (1–4C)alkyl, (1–4C)alkoxy, (1–4C)alkylamino, di-[(1–4C)alkyl]amino and (2–4C)alkanoylamino;

(e) $Q^1$ bears a substituent selected from amino-(1–4C)alkyl, (1–4C)alkylamino-(1–4C)alkyl, di-[(1–4C)alkyl]amino-(1–4C)alkyl, pyrrolidin-1-yl-(1–4C)alkyl, piperidino-(1–4C)alkyl, morpholino-(1–4C)alkyl, piperazin-1-yl-(1–4C)alkyl and 4-(1–4C)alkylpiperazin-1-yl-(1–4C)alkyl;

(f) m is 1 and $R^1$ is hydrogen; and (g) m is 1 and $R^1$ is (1–4C)alkoxy.

A preferred compound of the invention is a quinazoline compound of the formula I wherein $Q^1$ is 2-furyl, 3-furyl, 2-thienyl, 3-thienyl, 2-pyridyl, 3-pyridyl, 4-pyridyl, 2-oxazolyl, 4-oxazolyl, 5-isoxazolyl, 3-pyrazolyl, 1-imidazolyl, 2-imidazolyl, 4-imidazolyl, 2-thiazolyl, 4-thiazolyl, 5-isothiazolyl or 1,2,3-triazol-4-yl which optionally bears a substituent selected from methyl, aminomethyl, 2-aminoethyl, methylaminomethyl, 2-methylaminoethyl, dimethylaminomethyl, 2-dimethylaminoethyl, pyrrolidin-1-ylmethyl, 2-pyrrolidin-1-ylethyl, piperidinomethyl, 2-piperidinoethyl, morpholinomethyl, 2-morpholinoethyl, piperazin-1-ylmethyl, 2-piperazin-1-ylethyl, 4-methylpiperazin-1-ylmethyl and 2-(4-methylpiperazin-1-yl)ethyl;

m is 1 and $R^1$ is hydrogen or methoxy;

and $Q^2$ is phenyl which optionally bears 1, 2 or 3 substituents selected from fluoro, chloro, bromo, trifluoromethyl, cyano, methyl and methoxy;

or a pharmaceutically-acceptable acid-addition salt thereof.

A further preferred compound of the invention is a quinazoline compound of the formula I wherein $Q^1$ is 2-furyl, 3-furyl, 2-thienyl, 3-thienyl, 2-pyridyl, 3-pyridyl, 4-pyridyl, 4-oxazolyl, 4-thiazolyl or 1-imidazolyl which optionally bears a substituent selected from aminomethyl, morpholinomethyl and 2-morpholinoethyl;

m is 1 and $R^1$ is hydrogen or methoxy;

and $Q^2$ is phenyl which optionally bears 1 or 2 substituents selected from fluoro, chloro, bromo and methyl;

or a pharmaceutically-acceptable acid-addition salt thereof.

A specific especially preferred compound of the invention is the quinazoline derivative of the formula I:

4-(3-chloro-4-fluoroanilino)-7-(3-furyl)quinazoline, 4-(3-chloro-4-fluoroanilino)-7-(3-thienyl)quinazoline or 4-(3-chloro-4-fluoroanilino)-7-(5-morpholinomethylthien-3-yl)quinazoline;

or a pharmaceutically-acceptable acid-addition salt thereof.

A quinazoline compound of the formula I, or a pharmaceutically-acceptable salt thereof, may be prepared by any process known to be applicable to the preparation of chemically-related compounds. Suitable processes include, for example, those illustrated in European Patent Applications Nos. 0520722, 0566226, 0602851, 0635507 and 0635498, and International Patent Applications WO 96/15118 and WO 96/16960. Such processes, when used to prepare a quinazoline compound of the formula I, or a pharmaceutically-acceptable salt thereof, are provided as a further feature of the invention and are illustrated by the following representative examples in which, unless otherwise stated, $Q^1$, m, $R^1$ and $Q^2$ have any of the meanings defined hereinbefore for a quinazoline compound of the formula I. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

(a) The reaction, conveniently in the presence of a suitable base, of a quinazoline of the formula III

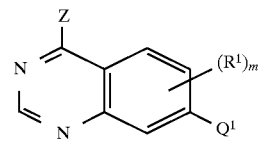

wherein Z is a displaceable group, with an aniline of the formula $Q^2$—$NH_2$.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal hydride, for example sodium hydride.

A suitable displaceable group Z is, for example, a halogeno, alkoxy, aryloxy or sulphonyloxy group, for example a chloro, bromo, methoxy, phenoxy, methanesulphonyloxy or toluene-4-sulphonyloxy group. The reaction is conveniently carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N- dimethylacetamide, N-methylpyrrolidin-2-one or dimethylsulphoxide. The reaction is conveniently carried out at a temperature in the range, for example, 10° to 250° C., preferably in the range 40° to 80° C.

The quinazoline compound of the formula I may be obtained from this process in the form of the free base or alternatively it may be obtained in the form of a salt with the acid of the formula H—Z wherein Z has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

(b) The reaction, conveniently in the presence of a suitable catalyst, of a quinazoline of the formula IV

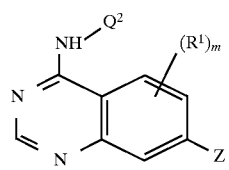

wherein Z is a displaceable group as defined hereinbefore, with an organoboron reagent of the formula $Q^1$—$B(L^1)(L^2)$ wherein each $L^1$ and $L^2$, which may be the same or different, is a suitable ligand.

A suitable value for the ligands $L^1$ and $L^2$ which are present on the boron atom include, for example, a hydroxy, (1–4C)alkoxy or (1–6C)alkyl ligand, for example a hydroxy, methoxy, ethoxy, propoxy, isopropoxy, butoxy, methyl, ethyl, propyl, isopropyl or butyl ligand. Alternatively the ligands $L^1$ and $L^2$ may be linked such that, together with the boron atom to which they are attached, they form a ring. For example, $L^1$ and $L^2$ together may define an oxy-(2–4C)alkylene-oxy group, for example an oxyethyleneoxy or oxytrimethyleneoxy group such that, together with the boron atom to which they are attached, they form a cyclic boronic acid ester group. Particularly suitable organoboron reagents include, for example, compounds of the formulae $Q^1$—$B(OH)_2$, $Q^1$—$B(OPr^i)_2$ and $Q^1$—$B(Et)_2$.

A suitable catalyst for the reaction includes, for example, a metallic catalyst such as a palladium(O), palladium(II), nickel(O) or nickel(II) catalyst, for example tetrakis(triphenylphosphine)palladium(O), palladium(II) chloride, palladium(II) bromide, bis(triphenylphosphine)palladium(II) chloride, tetrakis(triphenylphosphine)nickel(O), nickel(II) chloride, nickel(II) bromide or bis(triphenylphosphine)nickel(II) chloride. In addition a free radical initiator may conveniently be added, for example an azo compound such as azo(bisisobutyronitrile).

The reaction is conveniently carried out in the presence of a suitable inert solvent or diluent, for example an ether such as tetrahydrofuran, 1,4-dioxan or 1,2-dimethoxyethane, an aromatic solvent such as benzene, toluene or xylene, or an alcohol such as methanol or ethanol, and the reaction is conveniently carried out at a temperature in the range, for example 10° to 250° C., preferably in the range 60° to 120° C.

Organoboron reagents of the formula $Q^1$—$B(L^1)(L^2)$ may be obtained by standard procedures of organic chemistry which are within the ordinary skill of an organic chemist, for example by the reaction of an organometallic compound of the formula $Q^1$—M, wherein M is, for example, lithium or the magnesium halide portion of a Grignard reagent, with an organoboron compound of the formula Z—$B(L^1)(L^2)$ wherein Z is a displaceable group as defined hereinbefore. Preferably the compound of the formula Z—$B(L^1)(L^2)$ is, for example, boric acid or a tri-(1–4C)alkyl borate such as tri-isopropyl borate.

In an alternative procedure the organoboron compound of the formula $Q^1$—$B(L^1)(L^2)$ may be replaced with an organometallic compound of the formula $Q^1$—M wherein M is a metal atom or a metallic group (i.e. a metal atom bearing suitable ligands). Suitable values for the metal atom include, for example, lithium and copper. Suitable values for the metallic group include, for example, groups which contain a tin, silicon, zirconium, aluminium, magnesium or mercury atom. Suitable ligands within such a metallic group include, for example, hydroxy groups, (1–6C)alkyl groups such as methyl, ethyl, propyl, isopropyl and butyl groups, halogeno groups such as chloro, bromo and iodo groups, and (1–6C) alkoxy groups such as methoxy, ethoxy, propoxy, isopropoxy and butoxy groups. A particular organometallic compound of the formula $Q^1$—M is, for example, an organotin compound such as a compound of the formula $Q^1$—$SnBu_3$, an organosilicon compound such as a compound of the formula $Q^1$—$Si(Me)F_2$, an organozirconium compound such as a compound of the formula $Q^1$—$ZrCl_3$, an organoaluminium compound such as a compound of the formula $Q^1$—$AlEt_2$, an organomagnesium compound such as a compound of the formula $Q^1$—MgBr, or an organomercury compound such as a compound of the formula $Q^1$—HgBr.

(c) The reaction, conveniently in the presence of a suitable catalyst as defined hereinbefore, of a quinazoline of the formula V

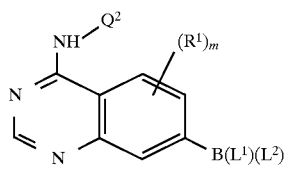

wherein each of $L^1$ and $L^2$, which may be the same or different, is a suitable ligand as defined hereinbefore, with a compound of the formula $Q^1$—Z wherein Z is a displaceable group as defined hereinbefore.

The reaction is conveniently carried out in a suitable inert solvent or diluent and at a suitable temperature in an analogous manner to the conditions described in paragraph (b) hereinbefore.

The quinazoline of the formula V may conveniently be obtained by analogous procedures to those described hereinbefore for the preparation of the organoboron reagent of the formula $Q^1$—$B(L^1)(L^2)$.

(d) For the production of those compounds of the formula I which possess an aminomethyl substituent, the reduction of a compound of the formula I which possesses a cyano substituent.

The reduction may be carried out by any of the many procedures known in the art for such transformations. A suitable reducing agent is, for example, an alkali metal aluminium hydride such as lithium aluminium hydride.

The reduction is conveniently carried out in a suitable inert solvent or diluent such as diethyl ether or tetrahydrofuran and at a temperature in the range, for example, 0° to 80° C., preferably in the range 15° to 50° C.

(e) For the production of those compounds of the formula I which possess an amino substituent, the reduction of a compound of the formula I which possesses a nitro substituent.

The reduction may conveniently be carried out by any of the many procedures known for such a transformation. The reduction may be carried out, for example, by the hydrogenation of a solution of the nitro compound in an inert solvent or diluent as defined hereinbefore in the presence of a suitable metal catalyst such as palladium or platinum. A further suitable reducing agent is, for example, an activated metal such as activated iron (produced by washing iron powder with a dilute solution of an acid such as hydrochloric acid). Thus, for example, the reduction may be carried out by heating a mixture of the nitro compound and the activated metal in a suitable solvent or diluent such as a mixture of water and an alcohol, for example, methanol or ethanol, to a temperature in the range, for example, 50° to 150° C., conveniently at or near 70° C.

When a pharmaceutically-acceptable salt of a quinazoline compound of the formula I is required, for example an acid-addition salt, it may be obtained, for example, by reaction of said compound with, for example, a suitable acid using a conventional procedure.

As stated hereinbefore the quinazoline compound defined in the present invention possesses anti-proliferative activity such as anti-cancer activity which is believed to arise from the Class I receptor tyrosine kinase inhibitory activity of the compound. These properties may be assessed, for example, using one or more of the procedures set out below:

(a) An in vitro assay which determines the ability of a test compound to inhibit the enzyme EGF receptor tyrosine kinase. Receptor tyrosine kinase was obtained in partially purified form from A-431 cells (derived from human vulval carcinoma) by the procedures described below which are related to those described by Carpenter et al., *J. Biol. Chem.*, 1979, 254, 4884, Cohen et al., *J. Biol. Chem.*, 1982, 257, 1523 and by Braun et al., *J. Biol. Chem.*, 1984, 259, 2051.

A-431 cells were grown to confluence using Dulbecco's modified Eagle's medium DMEM) containing 5% fetal calf serum (FCS). The obtained cells were homogenised in a hypotonic borate/EDTA buffer at pH 10.1. The homogenate was centrifuged at 400 g for 10 minutes at 0°–4° C. The supernatant was centrifuged at 25,000 g for 30 minutes at 0°–4° C. The pelleted material was suspended in 30 mM Hepes buffer at pH 7.4 containing 5% glycerol, 4 mM benzamidine and 1% Triton X-100, stirred for 1 hour at 0°–4° C., and recentrifuged at 100,000 g for 1 hour at 0°–4° C. The supernatant, containing solubilised receptor tyrosine kinase, was stored in liquid nitrogen.

For test purposes 40 µl of the enzyme solution so obtained was added to a mixture of 400 µl of a mixture of 150 mM Hepes buffer at pH 7.4, 500 µM sodium orthovanadate, 0.1% Triton X-100, 10% glycerol, 200 µl water, 80 µl of 25 mM DTT and 80 µl of a mixture of 12.5 mM manganese chloride, 125 mM magnesium chloride and distilled water. There was thus obtained the test enzyme solution.

Each test compound was dissolved in dimethylsulphoxide (DMSO) to give a 50 mM solution which was diluted with 40 mM Hepes buffer containing 0.1% Triton X-100, 10% glycerol and 10% DMSO to give a 500 µM solution. Equal volumes of this solution and a solution of epidermal growth factor (EGF; 20 µg/ml) were mixed.

[γ-$^{32}$P]ATP (3000 Ci/mM, 250 µCi) was diluted to a volume of 2 ml by the addition of a solution of ATP (100 µM) in distilled water. An equal volume of a 4 mg/ml solution of the peptide Arg-Arg-Leu-Ile-Glu-Asp-Ala-Glu-Tyr-Ala-Ala-Arg-Gly in a mixture of 40 mM Hepes buffer at pH 7.4, 0.1% Triton X-100 and 10% glycerol was added.

The test compound/EGF mixture solution (5 µl) was added to the test enzyme solution (10 µl) and the mixture was incubated at 0°–4° C. for 30 minutes. The ATP/peptide mixture (10 µl) was added and the mixture was incubated at 25° C. for 10 minutes. The phosphorylation reaction was terminated by the addition of 5% trichloroacetic acid (40 µl) and bovine serum albumin (BSA; 1 mg/ml, 5 µl). The mixture was allowed to stand at 4° C. for 30 minutes and then centrifuged. An aliquot (40 µl) of the supernatant was placed onto a strip of Whatman p 81 phosphocellulose paper. The strip was washed in 75 mM phosphoric acid (4×10 ml) and blotted dry. Radioactivity present in the filter paper was measured using a liquid scintillation counter (Sequence A). The reaction sequence was repeated in the absence of the EGF (Sequence B) and again in the absence of the test compound (Sequence C).

Receptor tyrosine kinase inhibition was calculated as follows:

$$\% \text{ Inhibition} = \frac{100 - (A - B)}{C - B} \times 100$$

The extent of inhibition was then determined at a range of concentrations of test compound to give an IC$_{50}$ value.

(b) An in vitro assay which determines the ability of a test compound to inhibit the EGF-stimulated growth of the human naso-pharyngeal cancer cell line KB.

KB cells were seeded into wells at a density of 1×10$^4$–1.5×10$^4$ cells per well and grown for 24 hours in DMEM supplemented with 5% FCS (charcoal-stripped). Cell growth was determined after incubation for 3 days by the extent of metabolism of MTT tetrazolium dye to furnish a bluish colour. Cell growth was then determined in the presence of EGF (10 ng/ml) or in the presence of EGF (10 ng/ml) and a test compound at a range of concentrations. An IC$_{50}$ value could then be calculated.

(c) An in vivo assay in a group of male rats which determines the ability of a test compound (usually administered orally as a ball-milled suspension in 0.5% polysorbate) to inhibit the stimulation of liver hepatocyte growth caused by the administration of the growth factor TGFα (400 µg/kg subcutaneously, usually dosed twice, 3 and 7 hours respectively after the administration of the test compound).

In a control group of rats, the administration of TGFα causes on average a 5-fold stimulation of liver hepatocyte growth.

Cell-growth in the control and test animals is determined as follows:

On the morning of the day after the dosing of the test compound (or 0.5% polysorbate in the control group), the animals are dosed with bromodeoxyuridine (BrdU; 100 mg/kg intraperitoneally). The animals are killed four hours later and the livers are excised. Slices are cut from each liver and the uptake of BrdU is determined by a conventional immunohistochemical technique similar to that described on pages 267 and 268 of an article by Goldsworthy et al. in Chemically Induced Cell Proliferation: Implications for Risk Assessment, Wiley-Liss Inc., 1991, pages 253–284. Further tests were carried out using a range of doses of the test compounds to allow the calculation of an approximate ED$_{50}$ value for the inhibition of liver hepatocyte proliferation as determined by inhibition of the uptake of BrdU.

(d) An in-vivo assay in a group of athymic nude mice (strain ONU:Alpk) which determines the ability of a test compound (usually administered orally as a ball-milled suspension in 0.5% polysorbate) to inhibit the growth of xenografts of the human vulval epidermoid carcinoma cell line A-431.

A-431 cells were maintained in culture in DMEM supplemented with 5% FCS and 2 mM glutamine. Freshly cultured cells were harvested by trypsinization and injected subcutaneously (10 million cells/0. 1 ml/mouse) into both flanks of a number of donor nude mice. When sufficient tumour material was available (after approximately 9 to 14 days), fragments of tumour tissue were transplanted into the flanks of recipient nude mice (test day 0). Generally, on the seventh day after transplantation (test day 7) groups of 7 to 10 mice with similar-sized tumours were selected and dosing of the test compound was commenced. Once-daily dosing of test compound was continued for a total of 13 days (test days 7 to 19 inclusive). In some studies the dosing of the test compound was continued beyond test day 19, for example to test day 26. In each case, on the following day the animals were killed and final tumour volume was calculated from measurements of the length and width of the tumours. Results were calculated as a percentage inhibition of tumour volume relative to untreated controls.

Although the pharmacological properties of the compounds of the formula I vary with structural change as expected, in general activity possessed by compounds of the formula I may be demonstrated at the following concentrations or doses in one or more of the above tests (a), (b), (c) and (d):

Test (a):—$IC_{50}$ in the range, for example, 0.01–1 $\mu$M;
Test (b):—$IC_{50}$ in the range, for example, 0.1–10 $\mu$M;
Test (c):—$ED_{50}$ in the range, for example, 1–100 mg/kg;
Test (d):—20 to 70% inhibition of tumour volume from a daily dose in the range, for example, 50 to 400 mg/kg.

Thus by way of example, the compound 4-(3-chloro-4-fluoroanilino)-7-(5-morpholinomethylthien-3-yl) quinazoline has an $IC_{50}$ of 0.042 $\mu$M in Test (a) and an $IC_{50}$ of 0.12 $\mu$M in Test (b).

According to a further aspect of the invention there is provided a pharmaceutical composition which comprises a quinazoline compound of the formula I, or a pharmaceutically-acceptable salt thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The quinazoline compound will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–100 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a quinazoline compound of the formula I as defined hereinbefore for use in a method of treatment of the human or animal body by therapy.

We have now found that the compounds of the present invention possess anti-proliferative properties which are believed to arise from their Class I (EGF type) receptor tyrosine kinase inhibitory activity. Accordingly the compounds of the present invention are expected to be useful in the treatment of diseases or medical conditions mediated alone or in part by Class I receptor tyrosine kinase enzymes, i.e. the compounds may be used to produce a Class I receptor tyrosine kinase inhibitory effect in a warm-blooded animal in need of such treatment. Thus the compounds of the present invention provide a method for treating the proliferation of malignant cells characterised by inhibition of Class I receptor tyrosine kinase enzymes, i.e. the compounds may be used to produce an anti-proliferative effect mediated alone or in part by the inhibition of Class I receptor tyrosine kinase. Accordingly the compounds of the present invention are expected to be useful in the treatment of cancer by providing an anti-proliferative effect, particularly in the treatment of Class I receptor tyrosine kinase sensitive cancers such as cancers of the breast, lung, colon, rectum, stomach, prostate bladder, pancreas and ovary. The compounds of the present invention are also expected to be useful in the treatment of other cell-proliferation diseases such as psoriasis, benign prostatic hypertrophy, atherosclerosis and restenosis.

Thus according to this aspect of the invention there is provided the use of a quinazoline compound of the formula I, or a pharmaceutically-acceptable salt thereof, as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of a quinazoline compound as defined immediately above.

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

The anti-proliferative treatment defined hereinbefore may be applied as a sole therapy or may involve, in addition to the quinazoline derivative of the invention, conventional radiotherapy or one or more other anti-tumour substances, for example cytotoxic or cytostatic anti-tumour substances, for example those selected from, for example, mitotic inhibitors, for example vinblastine, vindesine and vinorelbine; alkylating agents, for example cis-platin, carboplatin and cyclophosphamide; antimetabolites, for example 5-fluorouracil, tegafur, methotrexate, cytosine arabinoside and hydroxyurea, or, for example, one of the preferred antimetabolites disclosed in European Patent Application No. 239362 such as N-{5-[N-(3,4-dihydro-2-methyl-4-oxoquinazolin-6-ylmethyl)-N-methylamino]-2-thenoyl}-L-glutamic acid; intercalating antibiotics, for example adriamycin, mitomycin and bleomycin; enzymes, for example asparaginase; topoisomerase inhibitors, for example etoposide and camptothecin; biological response modifiers, for example interferon; and anti-hormones, for example antioestrogens such as tamoxifen, for example antiandrogens such as 4'-cyano-3-(4-fluorophenylsulphonyl)-2-hydroxy-2-methyl-3'-(trifluoromethyl)propionanilide or, for example LHRH antagonists or LHRH agonists such as goserelin, leuprorelin or buserelin and hormone synthesis inhibitors, for example aromatase inhibitors such as those disclosed in European Patent Application No. 0296749, for example 2,2'-[5-(1H-1,2,4-triazol-1-ylmethyl)-1,3-phenylene]bis(2-methylpropionitrile), and for example, inhibitors of 5α-reductase such as 17β-(N-tert-butylcarbamoyl)-4-aza-5α-androst-1-en-3-one. Such conjoint treatment may be achieved by way of the simultaneous, sequential or separate dosing of the individual components of the treatment. According to this aspect of the invention there is provided a pharmaceutical product comprising a quinazoline derivative of the formula I as defined hereinbefore and an additional anti-tumour substance as defined hereinbefore for the conjoint treatment of cancer.

As stated above the quinazoline compound defined in the present invention is an effective anti-cancer agent, which property is believed to arise from its Class I (EGF type) receptor tyrosine kinase inhibitory properties. Such a quinazoline compound of the invention is expected to possess a wide range of anti-cancer properties as Class I receptor tyrosine kinases have been implicated in many common human cancers such as leukaemia and breast, lung, colon, rectal, stomach, prostate, bladder, pancreas and ovarian cancer. Thus it is expected that a quinazoline compound of the invention will possess anti-cancer activity against these cancers. It is in addition expected that a quinazoline compound of the present invention will possess activity against a range of leukaemias, lymphoid malignancies and solid tumours such as carcinomas and sarcomas in tissues such as the liver, kidney, prostate and pancreas.

It is further expected that a quinazoline compound of the present invention will possess activity against other cell-proliferation diseases such as psoriasis, benign prostatic hypertrophy, atherosclerosis and restenosis.

It is also to be expected that a quinazoline compound of the invention will be useful in the treatment of additional disorders of cellular growth in which aberrant cell signalling by way of receptor tyrosine kinase enzymes, including as yet unidentified receptor tyrosine kinase enzymes, are involved. Such disorders include, for example, inflammation, angiogenesis, vascular restenosis, immunological disorders, pancreatitis, kidney disease and blastocyte maturation and implantation.

The invention will now be illustrated in the following non-limiting Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multilicities are shown as follows: s, singlet; d, doublet; t, triplet; m, multiplet, unless otherwise stated end-products of the formula I were dissolved in $CD_3SOCD_3$ for the determination of NMR values.

(vii) intermediates were not generally fully characterised and purity was assessed by thin layer chromatography (TLC), infra-red (IR) or NMR analysis;

(viii) the following abbreviations have been used:
DMF N,N-dimethylformamide;
DMA N,N-dimethylacetamide;
THF tetrahydrofuran;
DME 1,2-dimethoxyethane.

EXAMPLE 1

Tetrakis(triphenylphosphine)palladium(O) (0.06 g) was added to a stirred mixture of 7-bromo-4-(3-chloro-4-fluoroanilino)quinazoline hydrochloride salt (0.43 g), a saturated aqueous sodium bicarbonate solution (16 ml), di-isopropyl 3-thienylboronate and DME (28 ml). The resultant mixture was stirred and heated to 100° C. for 2 hours. The mixture was cooled to ambient temperature. A 5M aqueous sodium hydroxide solution (8 ml) and water were added in turn. The resultant precipitate was isolated and washed with water and with methylene chloride. The material was purified by column chromatography using increasingly polar mixtures of methylene chloride and methanol as eluent. There was thus obtained 4-(3-chloro-4-fluoroanilino)-7-(3-thienyl)quinazoline (0.25 g), m.p.>250° C.;

NMR Spectrum: 7.46 (t, 1H), 7.73 (m, 1H), 7.81 (m, 1H), 7.87 (m, 1H), 8.08 (m, 1H), 8.14 (d, 1H), 8.24 (m, 2H), 8.56 (d, 1H), 8.66 (s, 1H), 9.88 (s, 1H);

Elemental Analysis: Found C, 60.5; H, 3.3; N, 11.7; $C_{18}H_{11}ClFN_3S$ requires C, 60.8; H, 3.1; N, 11.8%.

The 7-bromo-4-(3-chloro-4-fluoroanilino)quinazoline hydrochloride salt used as a starting material was obtained as follows:

A mixture of 4-bromoanthranilic acid (5.4 g) and formamide (11 ml) was stirred and heated to 140° C. for 16 hours. The mixture was cooled to ambient temperature. Acetone was added and the precipitate was isolated and dried. There was thus obtained 7-bromo-3,4-dihydroquinazolin-4-one (5.4 g).

A mixture of the material so obtained, thionyl chloride (50 ml) and DMF (0.3 ml) was stirred and heated to reflux for 3 hours. The mixture was evaporated to give 7-bromo-4-chloroquinazoline hydrochloride salt which was used without further purification.

A mixture of a portion (4.38 g) of the material so obtained, 3-chloro-4-fluoroaniline (2.28 g) and isopropanol (100 ml) was stirred and heated to reflux for 2 hours. The mixture was filtered whilst hot. The solid so obtained was washed with acetone and dried. There was thus obtained 7-bromo-4-(3-chloro-4-fluoroanilino)quinazoline hydrochloride salt (3.3 g).

The di-isopropyl 3-thienylboronate used as a starting material was obtained as follows:

n-Butyllithium (1.6M in hexane, 1.6 ml) was added dropwise to a stirred solution of 3-bromothiophene (0.36 g) in THF (8 ml) which had been cooled to −78° C. Tri-isopropyl borate (0.63 ml) was added dropwise and the resultant mixture was stirred and allowed to warm to ambient temperature. The mixture was evaporated to give the required starting material which was used without further purification.

EXAMPLE 2

Using an analogous procedure to that described in Example 1, 7-bromo-4-(3-chloro-4-fluoroanilino)

quinazoline hydrochloride salt was reacted with di-isopropyl 3-furylboronate to give 4-(3-chloro-4-fluoroanilino)-7-(3-furyl)quinazoline in 37% yield, m.p. 249°–250° C.;

NMR Spectrum: 7.22 (d, 1H), 7.45 (s, 1H), 7.83 (t, 1H), 7.87 (m, 1H), 7.96 (m, 1H), 8.03 (d, 1H), 8.22 (m, 1H), 8.48 (s, 1H), 8.52 (d, 1H), 8.64 (s, 1H), 9.85 (s, 1H);

Elemental Analysis: Found C, 62.9; H, 3.0; N, 12.3; $C_{18}H_{11}ClFN_3O_{0.2}H_2O$ requires C, 63.0; H, 3.35; N, 12.2%.

The di-isopropyl 3-furylboronate used as a starting material was obtained by the reaction of 3-bromofuran and tri-isopropyl borate using an analogous procedure to that described in the portion of Example 1 which is concerned with the preparation of starting materials.

EXAMPLE 3

Using an analogous procedure to that described in Example 1, 7-bromo-4-(3-chloro-4-fluoroanilino) quinazoline hydrochloride salt was reacted with di-isopropyl 2-furylboronate to give 4-(3-chloro-4-fluoroanilino)-7-(2-furyl)quinazoline in 36% yield, m.p.>250° C.;

NMR Spectrum: 6.7 (m, 1H), 7.31 (d, 1H), 7.43 (t, 1H), 7.87 (m, 2H), 8.02 (m, 2H), 8.22 (m, 1H), 8.56 (d, 1H), 8.64 (s, 1H), 9.88 (s, 1H);

Elemental Analysis: Found C, 63.6; H, 3.2; N, 12.2; $C_{18}H_{11}ClFN_3O$ requires C, 63.6; H, 3.3; N, 12.4%.

The di-isopropyl 2-furylboronate used as a starting material was obtained as follows:

n-Butyllithium (1.6M in hexane, 3.08 ml) was added dropwise to a stirred solution of furan (0.28 g) in THF (6 ml) which had been cooled to 0° C. The resultant mixture was stirred at ambient temperature for 20 minutes. The mixture was cooled to −78° C. and tri-isopropyl borate (1.12 ml) was added dropwise. The mixture was allowed to warm to ambient temperature and was stirred for 2 hours. The mixture was evaporated to give the required starting material which was used without further purification.

EXAMPLE 4

A mixture of 4-chloro-7-(1-imidazolyl)quinazoline hydrochloride salt (0.58 g), 3-chloro-4-fluoroaniline (0.352 g) and isopropanol (15 ml) was stirred and heated to reflux for 2 hours. The mixture was cooled to ambient temperature and the precipitate was isolated and washed in turn with isopropanol and with diethyl ether. There was thus obtained 4-(3-chloro-4-fluoroanilino)-7-(1-imidazolyl)quinazoline (0.295 g);

NMR Spectrum: 7.18 (s, 1H), 7.48 (t, 1H), 7.87 (m, 1H), 8.05 (d, 1H), 8.1 (m, 2H), 8.23 (m, 1H), 8.58 (s, 1H), 8.67 (s, 1H), 8.68 (d, 1H), 9.97 (broad s, 1H);

Elemental Analysis: Found C, 56.4; H, 3.7; N, 18.8; $C_{17}H_{11}ClFN_5 1.35H_2O$ requires C, 56.1; H, 3.8; N, 19.2%.

The 4-chloro-7-(1-imidazolyl)quinazoline hydrochloride salt used as a starting material was obtained as follows:

A mixture of 7-fluoro-3,4-dihydroquinazolin-4-one (European Patent Application No. 0635498, Example 1 thereof; 10 g) and imidazole (20 g) was stirred and heated to 180° C. for 30 minutes. The mixture was poured into water and the resulting precipitate was isolated, washed with water and dried. There was thus obtained 7-(1-imidazolyl)-3,4-dihydroquinazolin-4-one (3 g);

NMR Spectrum: 7.16 (s, 1H), 7.32 (s, 1H), 7.88 (m, 1H), 8.01 (d, 1H), 8.17 (s, 1H), 8.24 (d, 1H), 8.54 (d, 1H).

A mixture of a portion (0.5 g) of the material so obtained, phosphoryl chloride (25 ml) and DMF (1 drop) was stirred and heated to reflux for 3 hours. The mixture was evaporated to give 4-chloro-7-(1-imidazolyl)quinazoline hydrochloride salt which was used without further purification.

EXAMPLE 5

Using an analogous procedure to that described in Example 1, 7-bromo-4-(3-chloro-4-fluoroanilino) quinazoline hydrochloride salt was reacted with di-isopropyl 5-morpholinomethylthien-3-ylboronate. The reaction mixture was cooled to ambient temperature and a 5M aqueous sodium hydroxide solution was added. The mixture was extracted with methylene chloride. The organic phase was washed with brine, dried and evaporated. The residue was purified by column chromatography using a 25:1 mixture of methylene chloride and methanol as eluent. There was thus obtained 4-(3-chloro-4-fluoroanilino)-7-(5-morpholinomethylthien-3-yl)quinazoline in 34% yield, m.p. 238°–240° C.;

NMR Spectrum: 3.6 (t, 4H), 7.45 (t, 1H), 7.63 (s, 1H), 7.88 (m, 1H), 8.03 (m, 2H), 8.13 (d, 1H), 8.23 (m, 1H), 8.54 (d, 1H), 8.64 (s, 1H), 9.88 (s, 1H);

Elemental Analysis: Found C, 60.4; H, 4.4; N, 12.0; $C_{23}H_{20}ClFN_4OS$ requires C, 60.7; H, 4.4; N, 12.3%.

The di-isopropyl 5-morpholinomethylthien-3-ylboronate used as a starting material was obtained as follows:

Sodium cyanoborohydride (2 g) was added portionwise to a stirred mixture of 4-bromo-2-thiophenecarbaldehyde (4.78 g), morpholine (2.1 g), glacial acetic acid (1.8 g) and ethanol (125 ml). The mixture was stirred at ambient temperature for 1 hour. The mixture was poured into a saturated aqueous sodium bicarbonate solution and extracted with methylene chloride. The organic phase was washed with brine and evaporated. The resultant oil was partitioned between a dilute (10%) aqueous hydrochloric acid solution and methylene chloride. The aqueous phase was basified by the addition of a saturated aqueous sodium bicarbonate solution and extracted with methylene chloride. The organic extract was dried ($MgSO_4$) and evaporated to give 4-bromo-2-morpholinomethylthiophene (3.2 g);

NMR Spectrum: 2.4 (t, 4H), 3.55 (t, 4H), 3.65 (s, 2H), 6.95 (d, 1H), 7.5 (d, 1H).

A portion (1.22 g) of the material so obtained was dissolved in THF (100 ml) and the solution was cooled to −78° C. Tri-isopropyl borate (0.963 g) and n-butyllithium (1.6M in hexane, 2.91 ml) were added in turn. The mixture was stirred at −78° C. for 30 minutes and then allowed to warm to ambient temperature. The mixture was evaporated to give di-isopropyl 5-morpholinomethylthien-3-ylboronate which was used without further purification.

EXAMPLE 6

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

-continued

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone | 2.25 |
| Magnesium stearate | 3.0 |
| (c) Tablet III | mg/tablet |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound X | 10 |
| Lactose Ph.Eur | 488.5 |
| Magnesium stearate | 1.5 |
| (e) Injection 1 | (50 mg/ml) |
| Compound X | 5.0% w/v |
| 1M Sodium hydroxide solution | 15.0% w/v |
| 0.1M flydrochloric acid (to adjust pH to 7.6) | |
| Polyethylene glycol 400 | 4.5% w/v |
| Water for injection to 100% | |
| (f) Injection II | (10 mg/ml) |
| Compound X | 1.0% w/v |
| Sodium phosphate BP | 3.6% w/v |
| 0.1M Sodium hydroxide solution | 15.0% v/v |
| Water for injection to 100% | |
| (g) Injection III | (1 mg/ml, buffered to pH6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note

The above formulations may be obtained by conventional procedures well known in the pharmaceutical art. The tablets (a)–(c) may be enteric coated by conventional means, for example to provide a coating of cellulose acetate phthalate.

What we claim is:

1. A quinazoline compound of the formula I

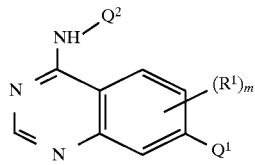

wherein $Q^1$ is a 5- or 6-membered heteroaryl moiety containing up to 3 heteroatoms selected from oxygen, nitrogen and sulphur, which heterocyclic moiety is a single ring or is fused to a benzo ring, and $Q^1$ optionally bears up to 3 substituents selected from halogeno, hydroxy, amino, trifluoromethyl, cyano, nitro, carboxy, carbamoyl, (1–4C)alkoxycarbonyl, (1–4C)alkyl, (1–4C)alkoxy, (1–4C)alkylamino, di-[(1–4C)alkyl]amino, pyrrolidin-1-yl, piperidino, morpholino, piperazin-1-yl, 4-(1–4C)alkylpiperazin-1yl, (2–4C)alkanoylamino, N-(1–4C)alkylcarbamoyl, N,N-di-[(1–4C)alkyl]carbamoyl, amino-(1–4C)alkyl, (1–4C)alkylamino-(1–4C)alkyl, di-[(1–4C)alkyl]amino-(1–4C)alkyl, pyrrolidin-1-yl-(1–4C)alkyl, piperidino-(1–4C)alkyl, morpholino-(1–4C)alkyl, piperazin-1-yl-(1–4C)alkyl, 4-(1–4C)alkylpiperazin-1-yl-(1–4C)alkyl, halogeno-(2–4C)alkoxy, hydroxy-(2–4C)alkoxy, (1–4C)alkoxy-(2–4C)alkoxy, amino-(2–4C)alkoxy, (1–4C)alkylamino-(2–4C)alkoxy, di-[(1–4C)alkyl]amino-(2–4C)alkoxy, pyrrolidin-1-yl-(2–4C)alkoxy, piperidino-(2–4C)alkoxy, morpholino-(2–4C)alkoxy, piperazin-1-yl-(2–4C)alkoxy, 4-(1–4C)alkylpiperazin-1-yl-(2–4C)alkoxy, (1–4C)alkylthio-(2–4C)alkoxy, (1–4C)alkylsulphinyl-(2–4C)alkoxy, (1–4C)alkylsulphonyl-(2–4C)alkoxy, halogeno-(2–4C)alkylamino, hydroxy-(2–4C)alkylamino, (1–4C)alkoxy-(2–4C)alkylamino, amino-(2–4C)alkylamino, (1–4C)alkylamino-(2–4C)alkylamino, di-[(1–4C)alkyl]amino-(2–4C)alkylamino, pyrrolidin-1-yl-(2–4C)alkylamino, piperidino-(2–4C)alkylamino, morpholino-(2–4C)alkylamino, piperazin-1-yl-(2–4C)alkylamino, 4-(1–4C)alkylpiperazin-1-yl-(2–4C)alkylamino, N-(1–4C)alkyl-halogeno-(2–4C)alkylamino, N-(1–4C)alkyl-hydroxy-(2–4C)alkylamino, N-(1–4C)alkyl-(1–4C)alkoxy-(2–4C)alkylamino, halogeno-(2–4C)alkanoylamino, hydroxy-(2–4C)alkanoylamino, (1–4C)alkoxy-(2–4C)alkanoylamino, (3–4C)alkenoylamino, (3–4C)alkynoylamino, amino-(2–4C)alkanoylamino, (1–4C)alkylamino-(2–4C)alkanoylamino, di-[(1–4C)alkyl]amino-(2–4C)alkanoylamino, pyrrolidin-1-yl-(2–4C)alkanoylamino, piperidino-(2–4C)alkanoylamino, morpholino-(2–4C)alkanoylamino, piperazin-1-yl-(2–4C)alkanoylamino and 4-(1–4C)alkylpiperazin-1-yl-(2–4C)alkanoylamino, and wherein any of the above-mentioned substituents comprising a $CH_2$ (methylene) group which is not attached to a halogeno, SO or $SO_2$ group or to a N, O or S atom optionally bears on said $CH_2$ group a substituent selected from hydroxy, amino, (1–4C)alkoxy, (1–4C)alkylamino and di-[(1–4C)alkyl]amino;

wherein m is 1 or 2 and each $R^1$ is independently hydrogen, halogeno, trifluoromethyl, hydroxy, amino, nitro, cyano, carboxy, carbamoyl, (1–4C)alkoxycarbamoyl, (1–4C)alkyl, (1–4C)alkoxy, (1–4C)alkylamino, di-[(1–4C)alkyl]amino, (2–4C)alkanoylamino, N-(1–4C)alkylcarbamoyl or N,N-di-[(1–4C)alkyl]carbamoyl;

and wherein $Q^2$ is phenyl which optionally bears up to 3 substituents selected from halogeno, trifluoromethyl, cyano, hydroxy, amino, nitro, carboxy, carbamoyl, (1–4C)alkoxycarbonyl, (1–4C)alkyl, (1–4C)alkoxy, (1–4C)alkylamino, di-[(1–4C)alkyl]amino, (2–4C)alkanoylamino, N-(1–4C)alkylcarbamoyl and N,N-di-(1–4C)alkylcarbamoyl;

or a pharmaceutically-acceptable salt thereof.

2. A quinazoline compound of the formula I as claimed in claim 1 wherein $Q^1$ is 2-furyl, 3-furyl, 2-thienyl, 3-thienyl, 2-pyridyl, 3-pyridyl, 4-pyridyl, 2-oxazolyl, 4-oxazolyl, 5-isoxazolyl, 3-pyrazolyl, 1-imidazolyl, 2-imidazolyl, 4-imidazolyl, 2-thiazolyl, 4-thiazolyl, 5-isothiazolyl or 1,2,3-triazol-4-yl which optionally bears a substituent selected from methyl, aminomethyl, 2-aminoethyl, methylaminomethyl, 2-methylaminoethyl, dimethylaminomethyl, 2-dimethylaminoethyl, pyrrolidin-1-ylmethyl, 2-pyrrolidin-1-ylethyl, piperidinomethyl, 2-piperidinoethyl, morpholinomethyl, 2-morpholinoethyl, piperazin-1-ylmethyl, 2-piperazin-1-ylethyl, 4-methylpiperazin-1-ylmethyl and 2-(4-methylpiperazin-1-yl)ethyl;

m is 1 and $R^1$ is hydrogen or methoxy;

and $Q^2$ is phenyl which optionally bears 1, 2 or 3 substituents selected from fluoro, chloro, bromo, trifluoromethyl, cyano, methyl and methoxy;

or a pharmaceutically-acceptable acid-addition salt thereof.

3. A quinazoline compound of the formula I as claimed in claim 1 wherein $Q^1$ is 2-furyl, 3-furyl, 2-thienyl, 3-thienyl, 2-pyridyl, 3-pyridyl, 4-pyridyl, 4-oxazolyl, 4-thiazolyl or 1-imidazolyl which optionally bears a substituent selected from aminomethyl, morpholinomethyl and 2-morpholinoethyl;

m is 1 and $R^1$ is hydrogen or methoxy;

and $Q^2$ is phenyl which optionally bears 1 or 2 substituents selected from fluoro, chloro, bromo and methyl;

or a pharmaceutically-acceptable acid-addition salt thereof.

4. The quinazoline derivative of the formula I as claimed in claim 1 selected from:
4-(3-chloro-4-fluoroanilino)-7-(3-furyl)quinazoline,
4-(3-chloro-4-fluoroanilino)-7-(3-thienyl)quinazoline and
4-(3-chloro-4-fluoroanilino)-7-(5-morpholinomethylthien-3-yl)quinazoline;
or a pharmaceutically-acceptable acid-addition salt thereof.

5. A process for the preparation of a quinazoline compound of the formula I, or a pharmaceutically-acceptable salt thereof, as claimed in any one of claims 1 to 4 which comprises:

(a) the reaction of a quinazoline of the formula III

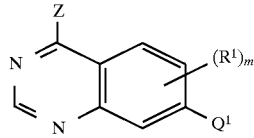

wherein Z is a displaceable group, with an aniline of the formula $Q^2$—$NH_2$;

(b) the reaction of a quinazoline of the formula IV

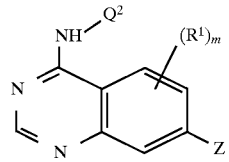

wherein Z is a displaceable group, with an organoboron reagent of the formula $Q^1$—$B(L^1)(L^2)$ wherein each $L^1$ and $L^2$, which may be the same or different, is a suitable ligand;

(c) the reaction of a quinazoline of the formula V

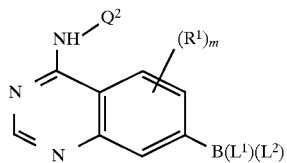

wherein each of $L^1$ and $L^2$, which may be the same or different, is a suitable ligand, with a compound of the formula $Q^1$—Z wherein Z is a displaceable group;

(d) for the production of those compounds of the formula I which possess an aminomethyl substituent, the reduction of a compound of the formula I which possesses a cyano substituent; or (e) for the production of those compounds of the formula I which possess an amino substituent, the reduction of a compound of the formula I which possesses a nitro substituent;

and when a pharmaceutically-acceptable salt of a quinazoline compound of the formula I is required it may be obtained by reaction of said compound using a conventional procedure.

6. A pharmaceutical composition which comprises a quinazoline compound of the formula I, or a pharmaceutically-acceptable salt thereof, as claimed in any one of claims 1 to 4 in association with a pharmaceutically-acceptable diluent or carrier.

7. A method for producing an anti-proliferative effect in a warm-blooded animal, such as man, in need of such treatment which comprises administering to said animal an effective amount of a quinazoline compound of the formula I, or a pharmaceutically-acceptable salt thereof, as claimed in any one of claims 1 to 4.

* * * * *